US011993638B2

(12) United States Patent
Potter et al.

(10) Patent No.: US 11,993,638 B2
(45) Date of Patent: *May 28, 2024

(54) GM-CSF MIMETICS AND METHODS OF MAKING AND USING SAME

(71) Applicant: The Regents of the University of Colorado, a body corporate, Denver, CO (US)

(72) Inventors: Huntington Potter, Denver, CO (US); Glenn Simon, Lakewood, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/589,154

(22) Filed: Jan. 31, 2022

(65) Prior Publication Data

US 2022/0153800 A1 May 19, 2022

Related U.S. Application Data

(63) Continuation of application No. 16/620,771, filed as application No. PCT/US2018/036736 on Jun. 8, 2018, now Pat. No. 11,267,859.

(60) Provisional application No. 62/517,744, filed on Jun. 9, 2017.

(51) Int. Cl.
| | | |
|---|---|---|
| A61K 38/00 | (2006.01) | |
| A61K 47/65 | (2017.01) | |
| C07K 14/535 | (2006.01) | |

(52) U.S. Cl.
CPC ............ *C07K 14/535* (2013.01); *A61K 47/65* (2017.08); *A61K 38/00* (2013.01)

(58) Field of Classification Search
CPC ...... A61K 38/00; A61K 47/64; C07K 14/535; C07K 2319/00
See application file for complete search history.

(56) References Cited

U.S. PATENT DOCUMENTS

| | | | | |
|---|---|---|---|---|
| 8,329,191 | B2 * | 12/2012 | Jo .......................... | A61K 47/60 424/193.1 |
| 11,267,859 | B2 * | 3/2022 | Potter .................. | C07K 14/535 |
| 2008/0292641 | A1 | 11/2008 | Sass et al. | |
| 2009/0197801 | A1 | 8/2009 | Berezin et al. | |
| 2013/0288908 | A1 | 10/2013 | Fujino et al. | |
| 2014/0030225 | A1 | 1/2014 | Cox | |

FOREIGN PATENT DOCUMENTS

| | | |
|---|---|---|
| WO | WO 8910403 | 11/1989 |
| WO | WO 2014066443 | 5/2014 |
| WO | WO 2018227142 | 12/2018 |

OTHER PUBLICATIONS

Dabritz et al. Molecular and Cellular Pediatrics (2015) 2:12. GM-CSF and the role of myeloid regulatory cells in the pathogenesis and treatment of Crohn's disease (Year: 2015).*
Ahmed, et al. "Pro-inflammatory Cytokine GM-CSF Improves Learning/Memory and Brain Pathology in Dp16 Down Syndrome Mice and Improves Learning/Memory in Wild-Type Mice." bioRxiv 2021.07.04.451073 (2021).
Boyd, et al. "GM-CSF Upregulated in Rheumatoid Arthritis Reverses Cognitive Impairment and Amyloidosis in Alzheimer Mice", J Alzheimers Dis., vol. 21, No. 2, pp. 507-518 (2010).
Brown, et al. "Mapping of human granulocyte-macrophage-colony-stimulating-factor domains interacting with the human granulocyte-macrophage—colony-stimulating-factor-receptor α-subunit", Eur J. Biochem, vol. 225, pp. 873-880 (1994).
Castellano, et al. "Human umbilical cord plasma proteins revitalize hippocampal function in aged mice", Nature, vol. 544, No. 7651, pp. 488-492 (2017).
Cedars Sinai. Accessed on Dec. 22, 2020 on https://www.cedars-sinai.org/programs/neurology-neurosurgery/conditions.html (2020).
Chen et al. "Inflammatory responses and inflammation-associated diseases in organs." Oncotarget, vol. 9, No. 6, pp. 7204-7218 (2018).
Dabritz et al. "GM-CSF and the role of myeloid regulatory cells in the pathogenesis and treatment of Crohn's disease" Molecular and Cellular Pediatrics, vol. 2, No. 1 pp. 1-8 (2015).
Dinarello, et al. "Grand Challenge in Inflammation", Front Immunol., vol. 3, p. 12 (2012).
Doherty, et al. "Site-Specific PEGylation of Engineered Cysteine Analogs of Recombinant Human Granulocyte-Macrophage Colony-Stimulating Factor", Bioconjug Chem., vol. 16, No. 5, pp. 1291-1298 (2005).
Hansen, et al. "The Structure of the GM-CSF Receptor Complex Reveals a Distinct Mode of Cytokine Receptor Activation", Cell, vol. 134, No. 3, pp. 496-507 (Aug. 2008).
Healthline—Understanding and Managing Chronic Inflammation. Accessed Dec. 29, 2020 on https://www.healthline.com/health/chronic-inflammation#effects-on-the-body (2018).
Hercus, et al. "The granulocyte-macrophage colony-stimulating factor receptor: linking its structure to cell signaling and its role in disease", Blood, vol. 114, No. 7, , pp. 1289-1298, (Aug. 2009).
Johns Hopkins medicine Accessed Dec. 23, 2020 at https://www.hopkinsmedicine.org/health/conditions-and-diseases/neurological-disorders (2020).
Kiran, et al. "Mental, Neurological, and Substance Use Disorders: Disease Control Priorities, Third Edition—Chapter 5: Neuroligical Disorders", vol. 4 (2016).
Komane, et al. "Diagnosis and Treatment of Neurological and Ischemic Disorders Employing Carbon Nanotube Technology", Journal of Nanomaterials (2016).
Lofti, et al. "Roles of GM-CSF in the Pathogenesis of Autoimmune Diseases: An Update", Front. Immunol., vol. 10, (Jun. 4, 2019).
Merck Manual—Delves, Peter: "Autoimmune Disorders", Accessed Jan. 7, 2021 at https://www.merckmanuals.com/home/immune-disorders/allergic-reactions-and-other-hypersensitivity-disorders/autoimmune-disorders.

(Continued)

*Primary Examiner* — Aradhana Sasan
*Assistant Examiner* — Mercy H Sabila
(74) *Attorney, Agent, or Firm* — Polsinelli PC

(57) ABSTRACT

The present invention provides novel GM-CSF constructs and methods of using the same. In certain embodiments, the constructs of the invention comprise certain peptide fragments from GM-CSF. In other embodiments, the invention provides certain GM-CSF peptides that act as GM-CSF mimetics.

25 Claims, 5 Drawing Sheets

Specification includes a Sequence Listing.

(56) References Cited

OTHER PUBLICATIONS

Merck Manual—Powell-Hamilton, Nina: "Down Syndrome (Trisomy 21)", Accessed Jul. 12, 2021 at https://my.clevelandclinic.org/health/diseases/17818-down-syndrome (2020).
Monfardini, et al. "Rational Design of Granulocyte-Macrophage Colony-stimulating Factor Antagonist Peptides", J Biological Chem; vol. 271, No. 6, pp. 2966-2971 (Feb. 1996).
Monfardini, et al. "Structure-based Design of Mimetics for Granulocyte-macrophage Colony Stimulating Factor (GM-CSF)", Current Pharmaceutical Design, vol. 8, No. 24, pp. 2185-2199, abstract only (2022).
Nishijima, et al. "A Human GM-CSF Receptor Expressed in Transgenic Mice Stimulates Proliferation and Differentiation of Hemopoietic Progenitors to All Lineages in Response to Human GM-CSF", Molecular Biology of the Cell; vol. 6, pp. 497-508 (May 1995).
Olson et al. "Granulocyte-macrophage colony-stimulating factor mRNA and Neuroprotective Immunity in Parkinson's disease", Biomaterials, vol. 272, 120786 (May 2021.
Pahwa, et al. "Chronic Inflammation", National Library of Medicine, NIH (Dec. 29, 2020).
Pang, et al. "Intracellular delivery mechanism and brain delivery kinetics of biodegradable cationic bovine serum albumin-conjugated polymersomes", International Journal of Nanomedicine; vol. 7, pp. 3421-3432 (2012).
Potter, et al. "Safety and efficacy of sargramostim (GM-CSF) in the treatment of Alzheimer's disease." Alzheimer's & Dementia: Translational Research & Clinical Interventions, vol. 7, No. 1, pp. 1-12 (2021).
Sharifi, et al. "Treatment of neurological and psychiatric disorders with deep brain stimulation; raising hopes and future challenges." Basic Clin Neurosci., vol. 4, No. 3, pp. 266-270 (2013).
Shultz, et al. "Granulocyte-Macrophage Colony-Stimulating Factor Is Neuroprotective in Experimental Traumatic Brain Injury", J Neurotrauma, vol. 31, pp. 976-983 (May 15, 2014).
Tamada, et al., "Homodimeric cross-over structure of the human granulocyte colony-stimulating factor (GCSF) receptor signaling complex", PNAS, vol. 103, No. 9, pp. 3135-3140 (Feb. 2006).
Upadhyay, "Drug Delivery Systems, CNS Protection, and the Blood Brain Barrier", BioMed Research International; pp. 1-37 (2014).
Walter, et al. "Three-dimensional structure of recombinant human granulocyte-macrophage colony-stimulating factor", J Mol Biology; vol. 224, pp. 1075-1085, Abstract only (1992).

* cited by examiner

GM-CSF MIMETICS AND METHODS OF MAKING AND USING SAME

CROSS REFERENCE TO RELATED APPLICATIONS

This Application is a continuation application of U.S. patent application Ser. No. 16/620,771, filed Dec. 9, 2019, which is a 371 national stage application of PCT Application No. PCT/US2018/036736 filed on Jun. 8, 2018, which claims priority to U.S. Provisional Application No. 62/517,744 filed Jun. 9, 2017. These applications are incorporated herein by reference in their entirety for all purposes.

SEQUENCE LISTING

The instant application contains a Sequence Listing which has been submitted in ASCII format via EFS-Web and is hereby incorporated by reference in its entirety. Said ASCII copy, created on Jun. 8, 2018, is named 373330-7072US1_SequenceListing_ST25.txt and is 8.20 kilobytes in size.

BACKGROUND OF THE INVENTION

GM-CSF (Granulocyte-Macrophage Colony-Simulating Factor) is a cytokine that regulates survival, proliferation, differentiation, and functional activation of hematopoietic and T cell function. Abnormalities in GM-CSF production or receptor function have been implicated in multiple pathologies such as rheumatoid arthritis, juvenile myelomonocytic leukemia, chronic myelomonocytic leukemia, and alveolar proteinosis. The GM-CSF receptor may play a role in the pathogenesis of chronic myeloid leukemia and myeloproliferative diseases by propagating survival and proliferation signals promoted by the abnormal expression of Bcr-Abl and JAK2 mutations, respectively. GM-CSF offers therapeutic promise to bolster antitumor immunity and innate immunity for treatment of Crohn's disease.

The receptor for GM-CSF is expressed at very low levels (100-1,000 per cell) on the surface of hematopoietic cells, and comprises GMRα chain/subunit and a βc chain/subunit. The GMRα subunit binds GM-CSF with low affinity ($K_D$=0.2–100 nM), but formation of a stable heterodimer with the βc subunit converts this to a high affinity interaction ($K_D$=100 pM) with low dissociation kinetics. Analysis of the crystal structure of the GM-CSF ternary complex revealed a 2:2:2 hexamer consisting of two GMRα subunits, two βc subunits, and two GM-CSF molecules. Furthermore, the crystal lattice revealed an unexpected dodecamer complex consisting of two hexameric complexes that are related by a crystallographic two-fold axis. Mutagenesis of the GM-CSF receptor at the dodecamer interface and functional studies reveals a profound effect on GM-CSF receptor signaling, and suggests that dodecamer formation may be required for full receptor activation and signaling.

Recombinant human GM-CSF (Leukine® or sargramostim) has been FDA approved since 1991 and safely used worldwide for leukopenia and in multiple stem cell transplantation settings. Recombinant human GM-CSF has also been used following induction chemotherapy in patients 55 years and older with acute myelogenous leukemia (AML) to shorten time to neutrophil recovery and to reduce the incidence of severe life-threatening infections. Recombinant human GM-CSF is further indicated for use in mobilization and following transplantation of autologous peripheral blood progenitor cells, for use in myeloid reconstitution after autologous bone marrow transplantation, for use in myeloid reconstitution after allogeneic bone marrow transplantation, and for use in bone marrow transplantation failure or engraftment delay. The standard treatment is five or seven days a week for three weeks, either as a subcutaneous injection or by infusion at a dose of 250 µg/m². Recombinant human GM-CSF has also been tested in the treatment of other conditions or diseases, such as Parkinson's Disease, and cognitive deficits observed in patients receiving chemotherapy or irradiation procedures, and it is also being tested in the treatment of Alzheimer's Disease.

Although sargramostim has proven to be a safe and beneficial drug for 20 years, that drug has serious limitations. Long-term sargramostim therapy often results in the formation of both GM-CSF binding autoantibodies and GM-CSF neutralizing autoantibodies. Not only do these autoantibodies reduce and potentially eliminate the efficacy of sargramostim treatment in humans, but animal models in which GM-CSF expression has been reduced (for example, by genetically knocking out the endogenous gene) exhibit severe pulmonary alveolar proteinosis (PAP), which also arises in humans and is associated with anti-GM-CSF antibodies. Further, because sargramostim is produced recombinantly in yeast, the final product may have different post-translational modifications in its polypeptide chain as compared to the endogenous human form of GM-CSF. Sargramostim contains a single amino acid difference from the endogenous human form(s) of GM-CSF, and that variation may underlie the production of the anti-GM-CSF autoantibodies. A molecule or treatment method that achieves the benefits of sargramostim, while reducing the likelihood of inducing anti-GM-CSF autoantibodies, would have immense clinical benefit. Another issue associated with sargramostim is that the product is relatively difficult to make, and it is quite expensive. A rough calculation suggests that treatment with sargramostim injections five days a week at 250 µg/m² for a year would cost over $50,000, which is most probably too high for general applicability.

There is thus a need in the art for identifying novel GM-CSF mimetics. In one aspect, these mimetics should be smaller in size and easier to synthesize than GM-CSF itself. In another aspect, these mimetics are GM-CSF receptor agonists. In yet other aspect, these mimetics should have at least one of the following favorable properties as compared to GM-CSF: improved bioavailability, improved stability, easier administration, improved blood brain barrier permeability, and improved oral bioavailability. The present invention addresses and meets this need.

BRIEF SUMMARY OF THE INVENTION

The invention provides certain constructs, which in certain embodiments comprise, consist essentially of, or consist of peptides.

In certain embodiments, the construct comprises $P^A$-LINKER-$P^B$-LINKER-$P^C$-LINKER-$P^D$ (1), wherein: each LINKER is independently a linker; two P groups selected from the group consisting of $P^A$-$P^D$ comprise the peptide of amino acid sequence of SEQ ID NO:7, or a biologically active fragment thereof; and two P groups selected from the group consisting of $P^A$-$P^D$ comprise the peptide of amino acid sequence of SEQ ID NO:8, or a biologically active fragment thereof; wherein (1) is not comprised within SEQ ID NOs:1-6.

In certain embodiments, $P^A$ and $P^C$ independently comprise the peptide of amino acid sequence of SEQ ID NO:7, and $P^B$ and $P^D$ comprise the peptide of amino acid sequence of SEQ ID NO:8.

In certain embodiments, $P^A$ and $P^D$ independently comprise the peptide of amino acid sequence of SEQ ID NO:7, and $P^B$ and $P^C$ comprise the peptide of amino acid sequence of SEQ ID NO:8.

In certain embodiments, $P^B$ and $P^D$ independently comprise the peptide of amino acid sequence of SEQ ID NO:7, and $P^A$ and $P^C$ comprise the peptide of amino acid sequence of SEQ ID NO:8.

In certain embodiments, $P^B$ and $P^C$ independently comprise the peptide of amino acid sequence of SEQ ID NO:7, and $P^A$ and $P^D$ comprise the peptide of amino acid sequence of SEQ ID NO:8.

In certain embodiments, at least one selected from the group consisting of $P^A$-$P^D$ comprises a peptide consisting of residues 11-X of SEQ ID NO:2, which optionally has the mutation R23L, wherein X is an integer selected from the group consisting of 24, 25, 26, 27, and 28.

In certain embodiments, at least one selected from the group consisting of $P^A$-$P^D$ comprises a peptide consisting of residues X-118 of SEQ ID NO:2, wherein X is an integer selected from the group consisting of 103, 104, 105, 106, 107, 108, 109, 110, and 111.

In certain embodiments, each LINKER is independently selected from the group consisting of $(CH_2CH_2O)_n$ and a peptide linker, wherein each occurrence of n is independently an integer ranging from 1 to 200.

In certain embodiments, at least one occurrence of the peptide linker is $(G_4S)_n$, $(G)_m$ or $(A)_m$, wherein n is an integer ranging from 1 to 6, and each occurrence of m is independently an integer ranging from 1 to 200.

In certain embodiments, the LINKER connecting the C-terminus of the peptide of amino acid sequence of SEQ ID NO:7 and the N-terminus of the peptide of amino acid sequence of SEQ ID NO:8 forms a hairpin.

In certain embodiments, the construct is selected from the group consisting of: Example a: QPWEHVNAIQEAR-LINKER-DFLLVIP-LINKER-QPWEHVNAIQEAR-LINKER-DFLLVIP (SEQ ID NO:7-LINKER-SEQ ID NO:8-LINKER-SEQ ID NO:7-LINKER-SEQ ID NO:8); Example b: QPWEHVNAIQEAR-LINKER-DFLLVIP-LINKER-DFLLVIP-LINKER-QPWEHVNAIQEAR (SEQ ID NO:7-LINKER-SEQ ID NO:8-LINKER-SEQ ID NO:8-LINKER-SEQ ID NO:7); Example c: DFLLVIP-LINKER-QPWEHVNAIQEAR-LINKER-QPWEHVNAIQEAR-LINKER-DFLLVIP (SEQ ID NO:8-LINKER-SEQ ID NO:7-LINKER-SEQ ID NO:7-LINKER-SEQ ID NO:8); Example d: DFLLVIP-LINKER-QPWEHVNAIQEAR-LINKER-DFLLVIP-LINKER-QPWEHVNAIQEAR (SEQ ID NO:8-LINKER-SEQ ID NO:7-LINKER-SEQ ID NO:8-LINKER-SEQ ID NO:7).

In certain embodiments, the construct is selected from the group consisting of: Example k: QPWEHVNAIQEAR {PEG6} DFLLVIP {PEG6} QPWEHVNAIQEAR {PEG6} DFLLVIP (SEQ ID NO:7-PEG6-SEQ ID NO:8-PEG6-SEQ ID NO:7-PEG6-SEQ ID NO:8); Example l: QPWEHVNAIQEAR {PEG6} DFLLVIP {PEG6} DFLLVIP {PEG6} QPWEHVNAIQEAR (SEQ ID NO:7-PEG6-SEQ ID NO:8-PEG6-SEQ ID NO:8-PEG6-SEQ ID NO:7); Example m: QPWEHVNAIQEAR {PEG4} DFLLVIP {PEG4} QPWEHVNAIQEAR {PEG4} DFLLVIP (SEQ ID NO:7-PEG4-SEQ ID NO:8-PEG4-SEQ ID NO:7-PEG4-SEQ ID NO:8); Example n: QPWEHVNAIQEAR {PEG8} DFLLVIP {PEG8} QPWEHVNAIQEAR {PEG8} DFLLVIP (SEQ ID NO:7-PEG8-SEQ ID NO:8-PEG8-SEQ ID NO:7-PEG8-SEQ ID NO:8);

In certain embodiments, the construct comprises a construct comprising $P^A$-LINKER-$P^B$ (2), wherein: LINKER is a linker; and $P^A$ and $P^B$ are independent selected from the group consisting of the peptide of amino acid sequence of SEQ ID NO:7, or a biologically active fragment thereof, and the peptide of amino acid sequence of SEQ ID NO:8, or a biologically active fragment thereof; wherein (2) is not comprised within SEQ ID NOs:1-6.

In certain embodiments, $P^A$ and $P^B$ comprise the peptide of amino acid sequence of SEQ ID NO:7.

In certain embodiments, $P^A$ and $P^B$ comprise the peptide of amino acid sequence of SEQ ID NO:8.

In certain embodiments, $P^A$ comprises the peptide of amino acid sequence of SEQ ID NO:7, and $P^B$ comprises the peptide of amino acid sequence of SEQ ID NO:8.

In certain embodiments, $P^B$ comprises the peptide of amino acid sequence of SEQ ID NO:7, and $P^A$ comprises the peptide of amino acid sequence of SEQ ID NO:8.

In certain embodiments, at least one selected from the group consisting of $P^A$-$P^B$ comprises a peptide consisting of residues 11-X of SEQ ID NO:2, which optionally has the mutation R23L, wherein X is an integer selected from the group consisting of 24, 25, 26, 27, and 28.

In certain embodiments, at least one selected from the group consisting of $P^A$-$P^B$ comprises a peptide consisting of residues X-118 of SEQ ID NO:2, wherein X is an integer selected from the group consisting of 103, 104, 105, 106, 107, 108, 109, 110, and 111.

In certain embodiments, the LINKER is selected from the group consisting of $(CH_2CH_2O)_n$ and a peptide linker, wherein each occurrence of n is independently an integer ranging from 1 to 200.

In certain embodiments, the peptide linker is $(G_4S)_n$, $(G)_m$ or $(A)_m$, wherein n is 1-6 and each occurrence of m is independently an integer ranging from 1 to 200.

In certain embodiments, the LINKER forms a hairpin.

In certain embodiments, the construct is selected from the group consisting of: Example e: QPWEHVNAIQEAR-LINKER-QPWEHVNAIQEAR (SEQ ID NO:7-LINKER-SEQ ID NO:7); Example f: DFLLVIP-LINKER-DFLLVIP (SEQ ID NO:8-LINKER-SEQ ID NO:8); Example g: QPWEHVNAIQEAR-LINKER-DFLLVIP (SEQ ID NO:7-LINKER-SEQ ID NO:8); Example h: DFLLVIP-LINKER-QPWEHVNAIQEAR (SEQ ID NO:8-LINKER-SEQ ID NO:7).

In certain embodiments, the construct is selected from the group consisting of: Example i: QPWEHVNAIQEAR {PEG6} DFLLVIP (SEQ ID NO:7-PEG6-SEQ ID NO:8); Example j: DFLLVIP {PEG6} QPWEHVNAIQEAR (SEQ ID NO:8-PEG6-SEQ ID NO:7).

In certain embodiments, the construct consists essentially, or consists, of an amino acid sequence selected from the group consisting of SEQ ID:7 and SEQ ID NO:8. In other embodiments, the construct is further chemically modified.

The invention further provides a method of treating and/or preventing a disease or disorder selected from the group consisting of leukopenia, rheumatoid arthritis, juvenile myelomonocytic leukemia, chronic myelomonocytic (or myeloid) leukemia, acute myelogenous leukemia, and alveolar proteinosis, in a subject. The invention further provides a method of promoting neurite outgrowth in a subject. The invention further provides a method of promoting myeloid reconstitution in a subject. The invention further provides a method of treating and/or preventing a neurodegenerative disease, neurological disorder, and/or traumatic brain injury (TBI) in a subject. The invention further provides a method of improving cognition, stabilizing cognition, and/or reversing loss of cognition in a subject. The invention further provides a method of increasing, or preventing decrease of, neutrophil levels in a subject. The invention further provides a method of immunizing a subject against an infection. The invention further provides a method of improving efficacy of immunotherapy treatment being administered to a subject. The invention further provides a method of reducing neuronal loss, preventing further neuronal loss, and/or reversing neuronal loss in a subject suffering from traumatic brain injury. The invention further provides a method of reducing or reversing autoimmunity in a subject. The invention further provides a method of reducing or reversing type I diabetes in a subject. The invention further provides a method of treating or reversing skin ulcers, Crohn's disease, and/or intestinal inflammation in a subject.

In certain embodiments, the method comprises administering a therapeutically effective amount of any construct of the invention to the subject. In other embodiments, the subject has received and/or is receiving a bone marrow transplantation and/or stem cell transplantation. In yet other embodiments, the subject has undergone chemotherapy and/or is undergoing chemotherapy. In yet other embodiments, the subject has developed "chemobrain" and/or has "chemobrain." In yet other embodiments, the subject has not undergone chemotherapy and/or is not undergoing chemotherapy. In yet other embodiments, the subject is, or is not, afflicted with at least one disease or disorder selected from the group consisting of Down Syndrome (DS), Alzheimer's Disease (AD), mild cognitive impairment, Parkinson's Disease, and cerebral palsy. In yet other embodiments, the construct is the only therapeutically effective compound administered to the subject, or wherein the construct is an adjuvant in the infection treatment being administered to the subject. In yet other embodiments, the infection is by a bacterium, fungus, and/or virus.

In certain embodiments, the construct is the only therapeutically effective compound administered to the subject.

In certain embodiments, the administration is performed by at least one route selected from the group consisting of subcutaneous, inhalational, oral, nasal, rectal, parenteral, sublingual, transdermal, transmucosal, intravesical, intrapulmonary, intraduodenal, intragastrical, intrathecal, epidural, intrapleural, intraperitoneal, intratracheal, otic, intraocular, intramuscular, intradermal, intra-arterial, intravenous, intrabronchial, inhalation, and topical. In other embodiments, the subject is a mammal. In yet other embodiments, the mammal is a human.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIGS. 2B-2C comprise flow cytometry plots from the TF-1 cells used to generate the data shown in FIG. 2A. The plots were gated by front and side scatter for singlets, then gated by DAPI, wherein DAPI-positive cells were dead and DAPI-negative cells were alive, and front scatter for live cells indicated in the selected region with the cell numbers represented below the plots.

FIG. 3B comprises a bar graph representing the % change in neutrophils for each group of mice shown in FIG. 3A. Error bars represent standard error of the mean. There is a significant difference between saline control and mimetic M4 ($P\leq0.046$) by a student's T-test. Paired T-test between 0h and 72h for both GM-CSF and M6 were statistically increased ($P<0.0019$ for GM-CSF and $P<0.0052$ for M6).

DETAILED DESCRIPTION OF THE INVENTION

Figure 1A:
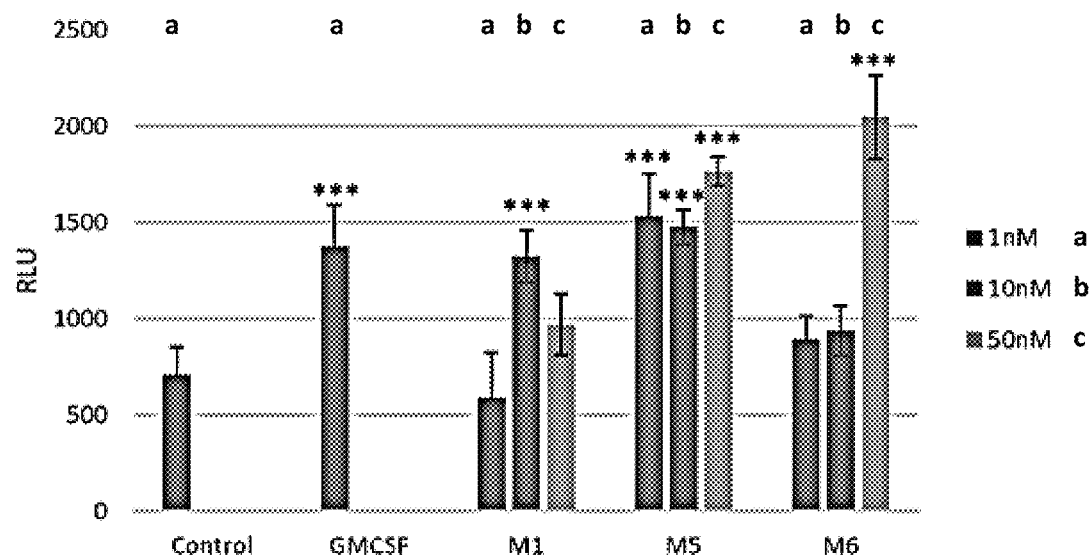
FIGS. 1A-1B comprise bar graphs illustrating use of the ATPlite assay to examine the viability of the GM-CSF-dependent human erythroleukemic cell line TF-1 (Hansen, et al., 2008, Cell 134(3):496-507) treated with GM-CSF mimetics of the invention (M1, M5, or M6; 1 nM, 10, nM, or 50 nM). TF-1 cells grown in the absence of GM-CSF (control) served as a negative control, and TF-1 cells grown in the presence of GM-CSF (GM-CSF; 0.7 nM) served as a positive control. This experiment showed that the GM-CSF mimetics M1, M5, and M6 show agonist activity at 24 h post-treatment (FIG. 1A) and 48 h post-treatment (FIG. 1B). Error bars represent standard error of the mean. *** indicates $P<0.0001$,* indicates $P\leq0.03$, compared to control.

The invention relates in one aspect to the unexpected discovery of novel GM-CSF mimetics. In certain embodiments, the mimetics of the invention are smaller in size and/or easier to synthesize than GM-CSF itself. In other embodiments, the mimetics of the invention are GM-CSF receptor agonists. In yet other embodiments, the mimetics of the invention have at least one of the following favorable properties as compared to GM-CSF: improved bioavailability, improved stability, easier administration, improved blood brain barrier permeability, and/or improved oral bioavailability. In yet other embodiments, the mimetics of the invention do not elicit development of GM-CSF autoantibodies when administered to a subject, such as a human. In yet other embodiments, the mimetics of the invention activate the GM-CSF receptor in the absence of GM-CSF itself, so as to elicit a benefit normally attributed to GM-CSF treatment.

In certain embodiments, the GM-CSF mimetics of the invention can be used in place of GM-CSF, in place of granulocyte colony stimulating factor (G-CSF), and/or in place of the combination of GM-CSF and G-CSF together. It should be noted that the recombinant protein drugs that are based on these two natural proteins (Leukine®/sagramostim for GM-CSF, and Neupogen®/filgastrim for G-CSF) are usually considered clinically interchangeable for the same indications. For example, GM-CSF and G-CSF used together improve cognition in patients suffering from cognitive decline due to chemotherapy (chemobrain), whereas G-CSF used alone does not improve cognition in patients suffering from chemobrain, and thus a GM-CSF mimetic can be used alone or together with G-CSF to replicate the beneficial effect(s) of GM-CSF and G-CSF used together.

In certain embodiments, the GM-CSF mimetics of the invention allow for an increase in immune and immune regulatory cells derived from the bone marrow or from other organs. In other embodiments, such immune and immune regulatory cells derived from the bone marrow or from other organs can serve, for example, as T-regulatory cells that reduce the generation of autoimmunity in a Parkinson's Disease patient or Alzheimer's Disease patient. In other embodiments, such immune and immune regulatory cells derived from the bone marrow or from other organs can serve, for example, as phagocytes that remove amyloid deposits in the brain of an Alzheimer's Disease patient. In yet other embodiments, the GM-CSF mimetics of the invention induce neurogenesis. In yet other embodiments, the GM-CSF mimetics of the invention induce neurite outgrowth. In yet other embodiments, the GM-CSF mimetics of the invention induce angiogenesis. In yet other embodiments, the GM-CSF mimetics of the invention protect a subject, such as an animal or a human, from sepsis and/or other infections. In yet other embodiments, the GM-CSF mimetics of the invention protect neurons from damage and/or death. In yet other embodiments, the GM-CSF mimetics of the invention provide benefits related to modification of microglial activity and/or synaptophysin expression.

The invention provides certain constructs comprising small peptide fragments of GM-CSF that are linked together through independently selected linkers. Such constructs are smaller in size and/or easier to synthesize than GM-CSF. The linkers can comprise, for example, polyethylene glycol chains (PEGs), peptides, and/or peptide nucleic acids (PNAs). In certain embodiments, the constructs of the invention comprise transferrin, or a biologically active fragment thereof, which allows for improved oral administration and improved blood-brain barrier permeability. In other embodiments, the constructs of the invention comprise AngioPep-2 (which promotes receptor-mediated transcytosis), HIV TAT, TAT49-57, transportan, and/or penetratin.

Substantial information is available regarding the structure of GM-CSF and of the GM-CSF receptor (Walter, et al., 1992, J. Mol. Biol. 224(4):1075-1085; Hansen, et al., 2008, Cell 134(3):496-507; both of which are incorporated in their entireties by reference). The minimal GM-CSF receptor is a heterodimer composed of one GMRα chain/subunit and one βc chain/subunit. Analysis of the crystal structure of the GM-CSF ternary complex revealed a 2:2:2 hexamer consisting of two GMRα subunits, two βc subunits, and two GM-CSF molecules (Hansen, et al., 2008, Cell 134(3):496-507). The hexamer includes interactions between GM-CSF and the GMRα subunit (this interaction surface is called Site 1). Specifically, loop residues 241-251 and 299-305 of the GMRα subunit interact with residues 11-23 and residues 112-118 of GM-CSF. The hexamer also includes interactions between GM-CSF and the βc subunit (this interaction surface is called Site 2). Mutagenesis studies show that the principal interaction between GM-CSF and the βc subunit occurs via a conserved glutamate (E21) in GM-CSF. The hexamer additionally includes interactions between the GMRα and βc subunits. Specifically, domain 2 of the GMRα subunit interacts extensively with domain 4 of the βc subunit, together with additional interacting surfaces between the two subunits (this interaction surface is called Site 3). Furthermore, analysis of the crystal lattice revealed an unexpected dodecamer complex consisting of two hexameric complexes related by a crystallographic two-fold axis. Specifically, the dodecamer complex assembles from two hexamers in a head-to-head orientation where the C-terminus tails of neighboring βc subunit domain 4's and GMRα subunit domain 2's are in close proximity (this interaction surface is called Site 4). Mutagenesis of the GM-CSF receptor at the dodecamer interface and functional studies reveals a profound effect on GM-CSF receptor signaling and suggests that dodecamer formation can be required for full receptor activation and signaling.

The present invention provides constructs that are agonists of the GM-CSF receptor, and thus can be used as GM-CSF mimetics.

In certain embodiments, the invention provides peptide M1 (amino acid sequence of SEQ ID NO:7), and peptide M2 (amino acid sequence of SEQ ID NO:8), which are active as a GM-CSF mimetic/agonist (FIGS. 1A-1B, FIGS. 2A-2C).

In certain embodiments, the constructs of the invention comprise peptide sequences corresponding to two regions within the GM-CSF amino acid sequence: the peptide of aa 28-40 of SEQ ID NO:1 (which corresponds to the peptide of amino acid sequence of SEQ ID NO:7 with Arg as the C-terminus residue, or the peptide of aa 11-23 of SEQ ID NO:2) and the peptide of aa 129-135 of SEQ ID NO:1 (which correspond to the peptide of amino acid sequence of SEQ ID NO:8, or the peptide of aa 112-118 of SEQ ID NO:2). In other embodiments, these peptide sequences are covalently connected through one or more linkers, so as to create a molecule that binds to and activates the GM-CSF receptor by interacting simultaneously with known regions within the GM-CSF receptor. In certain embodiments, the peptide of aa 28-40 of SEQ ID NO:1 has the mutation R40L (which corresponds to the mutation R23L in the peptide of aa 11-23 of SEQ ID NO:2; or the peptide of SEQ ID NO:7 with Leu as the C-terminus residue). In other embodiments, the constructs of the invention stabilize the GM-CSF receptor dodecamer complex, hexamer, and/or heterodimer.

The linker(s) used to covalently connect the GM-CSF peptide fragments can be amino acid sequences or a non-peptidic linker, such as but not limited to a polyethylene glycol, or any other linker of appropriate size and length that separates the GM-CSF peptide fragments in space, or any combinations thereof. In certain embodiments, the GM-CSF peptide fragments are synthesized chemically and are covalently connected through the linkers. In other embodiments, the GM-CSF peptide fragments are independently replaced by DNA aptamers selected by screening or by design to mimic the binding capacity of the GM-CSF peptide fragments for the GM-CSF receptor. In yet other embodiments, the GM-CSF peptide fragments are independently replaced by non-peptides, pseudo-peptides, and/or all D-amino acid peptide molecules having the same effective side chains capable of interacting with the GM-CSF receptor in the same and/or in a similar manner as the natural peptide fragment of GM-CSF, but with beneficial properties, such as but not limited to increased resistance to degradation. In yet other embodiments, the GM-CSF peptide fragments or replacement molecules are covalently connected in the same orientation as in the natural GM-CSF protein sequence, or are covalently connected in the reverse orientation as in the natural GM-CSF protein sequence.

The invention should not be construed to be limited to constructs comprising GM-CSF peptide fragments corresponding to the peptide of SEQ ID NO:7 and/or the peptide of SEQ ID NO:8. In certain embodiments, the constructs of the invention comprise GM-CSF peptide fragments, synthetic peptides, and/or other binding elements, that are independently longer or shorter than to the peptide of SEQ ID NO:7 and/or the peptide of SEQ ID NO:8, but have the same or similar effect of binding to the GM-CSF receptor and, when linked, of activating and/or stabilizing the GM-CSF receptor.

The constructs described herein can be administered to a human or an animal using the same administration forms used for GM-CSF; specifically, by infusion or subcutaneous injection. However, it is envisioned that the constructs of the invention can also be administered by nasal spray, so as to come in contact with the nasal epithelium and penetrate directly into the brain. Such administration would minimize the presence of the construct of the invention in blood, as would occur by subcutaneous injection or by intravenous infusion. In certain embodiments, constructs comprising a polyethylene glycol linker have longer half-lives and/or are more stable within the body, and can be effectively administered orally. In other embodiments, transferrin or other molecules and/or proteins are appended to the construct (either at its termini or internally), and the resulting construct has improved oral bioavailability and/or better blood-brain barrier permeability. Other methods for modifying the constructs of the invention to improve blood-brain barrier permeability are also well-known and can be employed herein (Pang, et al., 2014, Int. J. Nanomed. 7: 3421-3432; Upadhyay, 2014, Biomed. Res. Int. 869269). In yet other embodiments, the construct of the invention is encapsulated into nanoparticles, which can also be PEGylated; such modification can improve blood-brain barrier permeability. In yet other embodiments, linkage of the construct with a dendrimer improves the construct's blood-brain barrier permeability (see, for example, Srinageshwar, et al., 2017, Int. J. Mol. Sci. 18:628; Liu, et al., 2011, Int. J. Nanomed. 6:59-69).

More generally, the invention provides a method for generating a mimetic/receptor agonist molecule version of any ligand whose receptor-ligand interaction requires that both the receptor and the ligand be a dimer or a larger multimer. In addition to GM-CSF and the GM-CSF receptor, many other ligand-receptor interactions are most active following receptor dimerization (and subsequent hexameric and dodecameric complex formation, as in the case of GM-CSF and the GM-CSF receptor), and in certain cases actually require dimerization of the receptor to carry out their cellular function. For example, G-CSF functions through the formation of a complex with 2:2 stoichiometry (2 G-CSF: 2 G-CSF receptors) (Tamada, et al., 2006, Proc. Natl. Acad. Sci. USA 103(9):3135-3140). Because GM-CSF and G-CSF are medically interchangeable with respect to the use of Leukine® and Neupogen®, respectively, the mimetics for GM-CSF described herein can have similar medical benefits as Neupogen®. To generate a more specific G-CSF receptor agonist, the same approach as described herein to generate the GM-CSF mimetic can be carried out, and is considered part of this invention. Specifically, a linker comprising polyethylene glycol or any other linking molecule can be used to link the binding peptides, or synthetic versions thereof, of G-CSF together into a construct that can mimic the G-CSF dimer and effectively activate the G-CSF receptor complex.

Compounds and Compositions

Constructs of the invention are now exemplified in non-limiting manners. The peptide of amino acid sequence of SEQ ID NO:7 [QPWEHVNAIQEA(R/L); M1] and the peptide of amino acid sequence of SEQ ID NO:8 [DFLLVIP; M2] of the mature GM-CSF α chain bind to the GM-CSF receptor, and can be linked together to form a single construct (referred to herein as a "4-mer") wherein each half of the construct comprises both an M1 and an M2 GM-CSF peptide fragment (or other GM-CSF peptide fragment that binds to the GM-CSF receptor) joined by a linker (referred to herein as "L" and "LINKER").

Non-limiting examples of such constructs are M1-L-M2-L-M1-L-M2 [Example a]; M1-L-M2-L-M2-L-M1 [Example b]; M2-L-M1-L-M1-L-M2 [Example c]; and M2-L-M1-L-M2-L-M1 [Example d]). Each linker can be independently, for example but not limited to, a polyethylene glycol, and/or a peptide such as $(G)_{10}$ or $(A)_{10}$. The following molecules are non-limiting examples of such 4-mer constructs that mimic the active dimer of GM-CSF:

Example a: QPWEHVNAIQEAR-LINKER-DFLLVIP-LINKER-QPWEHVNAIQEAR-LINKER-DFLLVIP (SEQ ID NO: 7-LINKER-SEQ ID NO: 8-LINKER-SEQ ID NO: 7-LINKER-SEQ ID NO: 8); or Example b: QPWEHVNAIQEAR-LINKER-DFLLVIP-LINKER-DFLLVIP-LINKER-QPWEHVNAIQEAR (SEQ ID NO: 7-LINKER-SEQ ID NO: 8-LINKER-SEQ ID NO: 8-LINKER-SEQ ID NO: 7); or Example c: DFLLVIP-LINKER-QPWEHVNAIQEAR-LINKER-QPWEHVNAIQEAR-LINKER-DFLLVIP (SEQ ID NO: 8-LINKER-SEQ ID NO: 7-LINKER-SEQ ID NO: 7-LINKER-SEQ ID NO: 8); or Example d: DFLLVIP-LINKER-QPWEHVNAIQEAR-LINKER-DFLLVIP-LINKER-QPWEHVNAIQEAR (SEQ ID NO: 8-LINKER-SEQ ID NO: 7-LINKER-SEQ ID NO: 8-LINKER-SEQ ID NO: 7)

Alternatively, the peptide of S amino acid sequence of EQ ID NO:7 [QPWEHVNAIQEA(R/L); M1] and the peptide of amino acid sequence of SEQ ID NO:8 [DFLLVIP; M2] can be linked together to form a construct (referred to herein as a "2-mer") wherein each half of the construct comprises a GM-CSF peptide fragment (e.g., M1 or M2) joined by a linker (referred to herein as "L" and "LINKER").

Non-limiting examples of such constructs are: M1-L-M2; M2-L-M1; M1-L-M1; or M2-L-M2. Each linker can be independently, for example but not limited to, a polyethylene glycol, and/or a peptide such as $(G)_{10}$ or $(A)_{10}$. The following molecules are non-limiting examples of some such 2-mer constructs that mimic the active dimer of GM-CSF:

Example e: QPWEHVNAIQEAR-LINKER-QPWEHVNAIQEAR (SEQ ID NO: 7-LINKER-SEQ ID NO: 7); or Example f: DFLLVIP-LINKER-DFLLVIP (SEQ ID NO: 8-LINKER-SEQ ID NO: 8); or -continued

| | |
|---|---|
| Example g: | QPWEHVNAIQEAR-LINKER-DFLLVIP (SEQ ID NO: 7-LINKER-SEQ ID NO: 8); or |
| Example h: | DFLLVIP-LINKER-QPWEHVNAIQEAR (SEQ ID NO: 8-LINKER-SEQ ID NO: 7) |

Improved mimetic agonist structures with GM-CSF receptor binding can be achieved by using longer versions of peptide M1 (e.g., the peptide 11-28 of SEQ ID NO:2: QPWEHVNAIQEARRLLNL, optionally comprising the mutation R23L) and/or peptide M2 (residues 112-118) (e.g., the peptide 103-118 of SEQ ID NO:2: FESFKENLKDFLLVIP) to include the full a helices in those regions, or a combination of long and short peptides, which are also contemplated in this invention.

The choice of the linker molecule (for example, polypeptide chains are used as example linkers in Examples a-h) can be changed, based on a number of chemical or biological considerations, as is known in the field. For example, polyethylene glycol (PEG) can be easier to synthesize in various lengths than polypeptides, and has the advantage of being relatively biologically stable and non-immunogenic compared to polypeptides.

In certain embodiments, the linkers shown in Scheme 1 are contemplated in the invention, wherein a thiol (such as from a cysteine) forms a covalent adduct with the maleimido group, and a free amine (such as an N-terminus amino group) reacts with the succinimidyl ester to form an amide.

In other embodiments, linkers such as $H_2N—CH_2CH_2—[OCH_2CH_2]_n—COOH$, wherein n ranges from 2 to 30, can be used within the compounds and methods of the invention.

Scheme 1

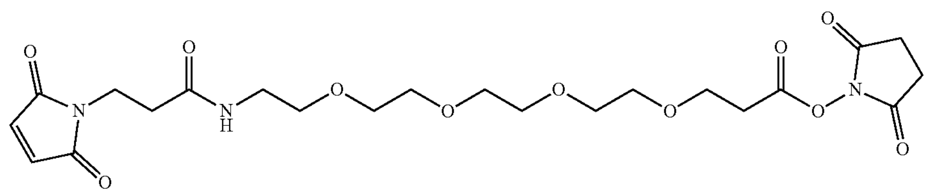

PEG 4 MW: 513.30 Spacer Arm: 24.6 Å

PEG 6 MW: 601.60 Spacer Arm: 32.5 Å

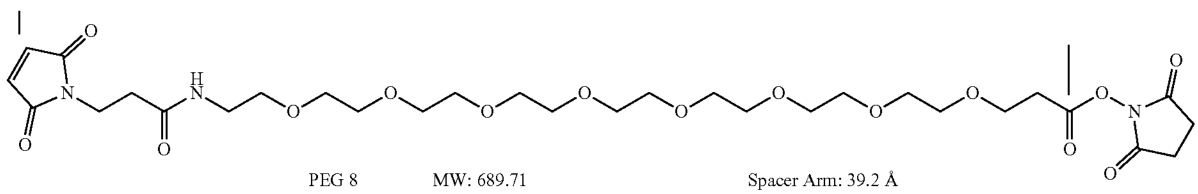

PEG 8 MW: 689.71 Spacer Arm: 39.2 Å

Linker Precursors Contemplated within the Invention

The present invention is not restricted to the particular length or structure of the linkers exemplified herein. Improved agonist activity or biological stability can be achieved by making the linkers longer or shorter and/or with varying properties, such as varying flexibilities. For example, as exemplified in Example a, the construct can comprise peptide M1 covalently linked to a hairpin linker, which is covalently linked to peptide M2, which covalently linked to a long flexible linker, which is covalently linked to peptide M1, which is covalently linked to a hairpin linker, which is covalently linked to peptide M2. In other examples, the last two peptide fragments can be reversed or in a different order as in Examples b-d. The simpler dimeric structures of Examples e-h can also be designed to use a hairpin linker, such as a tryptophan zipper, such as but not limited to those recited in Kim, et al., 2015, Chembiochem 16(1):43-46.

As a non-limiting example, such linkers have been used to generate the molecules shown in Scheme 2, named M1-M9 (claimed as Examples i-n, wherein n can be 4 (e.g. PEG4), 6 (e.g. PEG6), or 8 (e.g. PEG8), for example). M7 (Example o) uses the corresponding peptides from mouse GM-CSF and has activity for the mouse receptor, but M7 does not have activity for the human receptor.

Also contemplated is a GM-CSF mimetic comprising the two single peptide sequences (such as M1 or M2) linked as homodimers (i.e., M1-L-M1 or M2-L-M2), as in Examples e-f, or as heterodimers (i.e. M1-L-M2 or M2-L-M1), as in Examples g-h, wherein the LINKER can be PEG linkers (Examples i-j).

It is recognized that the teachings provided herein can be applied to GM-CSF-receptor binding fragments from the GM-CSF sequence from any animal (plus appropriate linkers) to generate receptor agonists useful for veterinary medicine or commercial purposes, and such constructs are also claimed. M9 (Example o) provides an example of a mouse GM-CSF mimetic.

```
                        Scheme 2:

Mimetic 1       QPWEHVNAIQEAR (SEQ ID NO: 7)
(M1):

Mimetic 2       DFLLVIP (SEQ ID NO: 8)
(M2):

Mimetic 3       QPWEHVNAIQEAR {PEG6} DFLLVIP
(M3)-Example    (SEQ ID NO: 7-PEG6-SEQ ID NO: 8)
i:

Mimetic 4       DFLLVIP {PEG6} QPWEHVNAIQEAR
(M4)-Example    (SEQ ID NO: 8-PEG6-SEQ ID NO: 7)
j:

Mimetic 5       QPWEHVNAIQEAR {PEG6} DFLLVIP {PEG6}
(M5)-Example    QPWEHVNAIQEAR {PEG6} DFLLVIP
k:              (SEQ ID NO: 7-PEG6-SEQ ID NO: 8-
                PEG6-SEQ ID NO: 7-PEG6-SEQ ID NO: 8)

Mimetic 6       QPWEHVNAIQEAR {PEG6} DFLLVIP {PEG6}
(M6)-Example    DFLLVIP {PEG6} QPWEHVNAIQEAR
l:              (SEQ ID NO: 7-PEG6-SEQ ID NO: 8-
                PEG6-SEQ ID NO: 8-PEG6-SEQ ID NO: 7)

Mimetic 7       QPWEHVNAIQEAR {PEG4} DFLLVIP {PEG4}
(M7)-Example    QPWEHVNAIQEAR {PEG4} DFLLVIP
m:              (SEQ ID NO: 7-PEG4-SEQ ID NO: 8-
                PEG4-SEQ ID NO: 7-PEG4-SEQ ID NO: 8)

Mimetic 8       QPWEHVNAIQEAR {PEG8} DFLLVIP {PEG8}
(M8)-Example    QPWEHVNAIQEAR {PEG8} DFLLVIP
n:              (SEQ ID NO: 7-PEG8-SEQ ID NO: 8-
                PEG8-SEQ ID NO: 7-PEG8-SEQ ID NO: 8)

Mimetic 9       RPWKHVEAIKEAL {PEG6} TFLTDIP
(M9, mouse)-    {PEG6} RPWKHVEAIKEAL {PEG6} TFLTDIP
Example o:      (SEQ ID NO: 9-PEG6-SEQ ID NO: 10-
                PEG6-SEQ ID NO: 9-PEG6-SEQ ID NO: 10)
```

GM-CSF mimetics M1-M8, comprising human GM-CSF peptide fragments M1 & M2 as well as M1 & M2 with various PEG linkers. Also shown is mimetic M9, comprising the corresponding peptide fragments from mouse GM-CSF. Molecules M3-M9 correspond to Examples i-n, respectively.

The invention further contemplates chemical modifications of the constructs described herein, wherein such modifications can provide additional useful features, such as, for example, increased binding affinity for the receptor, increased stability in biological fluids, increased oral availability, increased ability to cross the blood-brain barrier, and so forth. Many such modifications of peptide-based biologically active molecules are known in the art. In a non-limiting example, a method of adding stability (and even oral availability by promoting stability in the digestive system) is to use a mixture of α and β amino acids in the peptide regions of the GM-CSF mimetics. Introduction of β amino acids can be beneficial because they tend to promote the folding/stability of the adjacent amino acids as an α-helix, which is the secondary structure that the receptor-binding peptides assume in the combined crystal structure of GM-CSF and the GM-CSF receptor, and which is thus likely to promote, stabilize, and/or be necessary for receptor binding and activation. Other stability-promoting modifications include the addition of fatty acids, a small molecule binder of transthyretin, and/or a short PEG to the ends of the peptide chains of the constructs. Further examples comprise any methylated, C-amidated, N-acetylated, glycosylated, deglycosylated and/or partially glycosylated analogue or derivative thereof.

Also contemplated are GM-CSF mimetics in which the amino acid cysteine has been added in one or more locations or used in place of one or more natural amino acids to change the features of GM-CSF, such as stability in the body or ability to cross the blood-brain barrier, or which have been used as the site(s) of addition of polyethylene glycol (such as those recited in Doherty, et al., 2005, Bioconjug Chem. 16(5):1291-1298). For example, one or more of the synthetic fragments of GM-CSF (i.e., M1, M2, and/or the longer versions thereof) can be used to replace one or more loops in a cyclotide scaffold, a circular amino acid structure stabilized by disulfide bonds or other bonds. Such structures are stable, sometimes orally available, and able to present the peptide fragments in a stable conformation designed to optimize receptor binding. The entire mimetic can also by cyclized to improve stability, possibly with the inclusion of an additional linker between the ends of the current examples.

It may also be useful to include a "staple" in one or more of the peptide segments of the mimetics so as to stabilize the peptides in the active α-helix conformation and thus increase their affinity for the receptor. The staple should connect parts of the α-helix not directly involved in receptor binding. The staple may comprise a hydrocarbon. The α-helix conformation of GM-CSF-derived peptides in the mimetic can also be stabilized by N-terminus caps, or by other forms of side chain cross-links, including disulfides, thioethers, and lactams.

Salts

The compounds described herein may form salts with acids or bases, and such salts are included in the present invention. In one embodiment, the salts are pharmaceutically acceptable salts. The term "salts" embraces addition salts of free acids or bases that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification and/or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, galacturonic acid, glycerophosphonic acids, and saccharin (e.g., saccharinate, saccharate). Salts may be comprised of a fraction of one, one, or more than one molar equivalent of acid or base with respect to any compound of the invention.

Suitable pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Methods

The present invention provides methods of using the GM-CSF constructs of the invention. In certain embodiments, the constructs of the invention can be used in any method envisioned for GM-CSF or a recombinant form thereof.

In certain embodiments, the GM-CSF constructs of the invention can be used to treat and/or prevent a disease or disorder selected from the group consisting of leukopenia, rheumatoid arthritis, juvenile myelomonocytic leukemia, chronic myelomonocytic (or myeloid) leukemia, acute myelogenous leukemia, and alveolar proteinosis.

In certain embodiments, the GM-CSF constructs of the invention can be used to promote neurite outgrowth in a subject.

In certain embodiments, the GM-CSF constructs of the invention can be used to promote myeloid reconstitution in a subject. In other embodiments, the subject has received and/or is receiving a bone marrow transplantation and/or stem cell transplantation.

In certain embodiments, the GM-CSF constructs of the invention can be used to treat and/or prevent a neurodegenerative disease and/or traumatic brain injury (TBI) in a subject.

In certain embodiments, the GM-CSF constructs of the invention can be used to improve cognition, stabilize cognition, and/or reverse loss of cognition in a subject In certain embodiments, the subject is not afflicted with DS. In other embodiments, the subject is afflicted with DS.

In certain embodiments, the subject is not afflicted with Alzheimer's Disease (AD). In other embodiments, the subject is afflicted with AD.

In certain embodiments, the subject is not afflicted with mild cognitive impairment. In other embodiments, the subject is afflicted with mild cognitive impairment In certain embodiments, the subject is not afflicted with Parkinson's disease. In other embodiments, the subject is afflicted with Parkinson's disease.

In certain embodiments, the subject is not afflicted with cerebral palsy. In other embodiments, the subject is afflicted with cerebral palsy.

In certain embodiments, the subject has not undergone chemotherapy. In other embodiments, the subject is not undergoing chemotherapy. In yet other embodiments, the subject has not developed "chemobrain", and/or does not have "chemobrain", due to a prior or concomitant chemotherapy treatment.

In certain embodiments, the subject does not have amyloid deposits in the brain. In yet other embodiments, the subject has amyloid deposits in the brain.

In certain embodiments, because the constructs of the invention are mimetics of GM-CSF, they can be used in methods where GM-CSF has demonstrated activity, for example as a bone marrow stimulant, as an anti-neutropenia drug, and as a treatment against neurodegeneration, for example Alzheimer's Disease and Parkinson's Disease (Boyd, et al., 2010, J. Alzheimers Dis. 21(2):507-518; Choudhury, et al., 2011, Brain Behav 1(1): 26-43; Mangano, et al., 2011, Neurobiol Dis 43(1):99-112; Kosloski, et al., 2013, J Neuroimmunol 265(1-2): 1-10; Gendelman, et al., 2017, NPJ Parkinsons Dis 3:10; Kiyota, et al., 2018, J Neuroimmunol 319: 80-92; Schutt, et al., 2018, Mol Neurodegener 13(1): 26).

In certain embodiments, like GM-CSF, the constructs of the invention can be used as a stand-alone therapy or as an adjuvant in active and potentially passive immunization against a range of infectious disease targets, including bacteria, fungi, and viruses. In other embodiments, the GM-CSF constructs of the invention help maintain immune homeostasis, for example, during an inflammatory insult. For example, in humans, GM-CSF has been effective in combating fungal infections together with antifungal drugs (Goldman, et al., 2016, Med. Mycol. Case Rep. 11:40-43) and as a stand-alone therapy, or together with antibiotics, for generalized sepsis (Mathias, et al., 2015, Medicine (Baltimore) 94(50):e2044) or gram-negative bacterial infections (Meisel, et al., 2009, Am. J. Respir. Crit. Care Med. 180(7): 640-648; Hutchins, et al., 2014, Trends Mol. Med. 20(4): 224-233; Xu, et al., 2015, Hepatol. Int. 9(1):28-34). GM-CSF has also been effective in enhancing the effectiveness of influenza vaccination (Littauer, et al., 2018, J. Control Release 276:1-16).

In certain embodiments, like GM-CSF, the constructs of the invention can be used to improve cognition in cancer patients, to improve survival of melanoma patients, and to serve as an effective adjuvant in cancer immunotherapy. For example, GM-CSF has been shown to improve cognition in cancer patients (Jim, et al., 2012, Brain Disord. Ther. 1(1)), to improve survival of melanoma patients (Grotz, et al., 2014, Am. J. Clin. Oncol. 37(5):467-472; Hughes, et al., 2014, Oncolytic Virother 3:11-20; Hoeller, et al., 2016, Cancer Immunol. Immunother. 65(9):1015-1034), and to serve as an effective adjuvant in some cancer immunotherapy (Miyasaka, et al., 1994, Stroke 25(2):504-507; Aliper, et al., 2014, Cancer Med. 3(4):737-746).

In certain embodiments, like GM-CSF, the constructs of the invention can be used to reduce neuronal loss in traumatic brain injury. For example, GM-CSF has also been shown to reduce neuronal loss in animal models of traumatic brain injury (Nishihara, et al., 2011, Exp. Neurol. 229(2): 507-516; Shultz, et al., 2014, J. Neurotrauma 31(10):976-983; Kelso, et al., 2015, J. Neuroimmunol. 278:162-173).

In certain embodiments, like GM-CSF, the constructs of the invention can be used to interfere with or reverse autoimmunity, induce immune tolerance, and/or treat or prevent type I diabetes. For example, GM-CSF has been shown to interfere with or reverse autoimmunity or to induce immune tolerance in animal models (Bhattacharya, et al., 2015, Cytokine 75(2):261-271), for example, in myasthenia gravis models (Sheng, et al., 2006, J. Immunol. 177(8): 5296-5306; Sheng, et al., 2008, Clin. Immunol. 128(2):172-180) and one human patient with myasthenia gravis (Rowin, et al., 2012, Muscle Nerve 46(3):449-453). GM-CSF has also been shown to prevent type 1 diabetes in animal models (Gaudreau, et al., 2007, J. Immunol. 179(6):3638-3647; Cheatem, et al., 2009, Clin. Immunol. 131(2):260-270).

In certain embodiments, like GM-CSF, the constructs of the invention can be used to treat or prevent skin ulcers, Crohn's disease, and/or intestinal inflammation. For example, local injection of GM-CSF in humans has been used to heal skin ulcers, especially in diabetic patients (Remes, et al., 1999, J. Diabetes Complications 13(2):115-118; Bianchi, et al., 2002, J. Eur. Acad. Dermatol. Venereol. 16(6):595-598; Evans & Atherton, 2002, Br. J. Dermatol. 147(5):1023-1025). GM-CSF is beneficial in the treatment of animal models of Crohn's disease and reduces intestinal inflammation in humans (Dabritz, 2015, Mol. Cell Pediatr. 2(1):12).

In all of these applications, the constructs of the invention can serve as an inexpensive, easily synthesized, and similarly efficacious alternative to GM-CSF.

In certain embodiments, the construct is the only therapeutically effective compound administered to the subject. In other embodiments, the construct is the only therapeutically effective compound administered to the subject in a sufficient amount to treat, manage, and/or prevent the disorder or disease.

In certain embodiments, the administration is performed by at least one route selected from the group consisting of inhalational, oral, nasal, rectal, parenteral, sublingual, transdermal, transmucosal, intravesical, intrapulmonary, intraduodenal, intragastrical, intrathecal, epidural, intrapleural, intraperitoneal, intratracheal, otic, intraocular, subcutaneous, intramuscular, intradermal, intra-arterial, intravenous, intrabronchial, inhalation, and topical. In other embodiments, the subject is a mammal. In yet other embodiments, the mammal is a human.

The invention further provides a kit comprising a GM-CSF mimetic construct of the invention or any biologically active derivative or analogue thereof, an applicator and instructional material for use thereof, wherein the instructional material comprises instructions for treating, managing, and/or preventing the disorder or disease contemplated herein.

Combination and Concurrent Therapies

In certain embodiments, the compounds of the invention are useful in the methods of present invention when used concurrently with at least one additional compound useful for preventing and/or treating diseases and/or disorders contemplated herein. In other embodiments, the compounds of the invention are useful in the methods of present invention in combination with at least one additional compound useful for preventing and/or treating diseases and/or disorders contemplated herein.

These additional compounds may comprise compounds of the present invention or other compounds, such as commercially available compounds, known to treat, prevent, or reduce the symptoms of diseases and/or disorders contemplated herein, and/or improving normal cognition. In certain embodiments, the combination of at least one compound of the invention or a salt thereof, and at least one additional compound useful for preventing and/or treating diseases and/or disorders contemplated herein, or a person not exhibiting a disease or disorder such as those contemplated herein, has additive, complementary or synergistic effects in the prevention and/or treatment of diseases and/or disorders contemplated herein, or improving normal function not reduced or hampered by a disease or disorder such as those contemplated herein.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326), the median-effect equation (Chou & Talalay, 1984, Adv. Enzyme Regul. 22: 27-55), and through the use of isobolograms (Tallarida & Raffa, 1996, Life Sci. 58: 23-28). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention, or to improve function in an individual not suffering from a disease or disorder such as those contemplated herein. Dosage regimens may be adjusted to provide the optimum and/or beneficial therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic and/or beneficial response for a particular patient, composition, and mode of administration, without being toxic to the patient.

The therapeutically effective amount or dose of a compound of the present invention depends on the age, sex, and weight of the patient, the current medical condition of the patient and the progression of a disease or disorder, or the desired level of improved function, contemplated in the invention.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic and/or beneficial effect and gradually increase the dosage until the desired effect is achieved.

A suitable dose of a compound of the present invention may be in the range of from about 0.001 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3,050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, or less than about 0.05 mg, or less than about 0.005 mg, and any and all whole or partial increments thereof.

In one embodiment, the compounds and/or compositions of the invention are administered to the patient in dosages that range from one to five times per day or more. In another embodiment, the compositions of the invention are administered to the patient in a range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the compound and/or composition of the invention is optionally given continuously; alternatively, the dose of compound and/or composition being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In one embodiment, patients require intermittent treatment on a long-term basis upon any recurrence of symptoms.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal and the like. In many cases, it is preferable to include isotonic agents, for example, sugars, sodium chloride, or polyalcohols such as mannitol and sorbitol, in the composition.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for any suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring, and/or aromatic substances and the like. They may also be combined where desired with other active agents, e.g., analgesic agents.

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, intratracheal, otic, intraocular, subcutaneous, intramuscular, intradermal, intraarterial, intravenous, intrabronchial, inhalation, and topical administration.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release, and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

As used herein, the articles "a" and "an" are used to refer to one or to more than one (i.e., to at least one) of the grammatical object of the article. By way of example, "an element" means one element or more than one element.

As used herein, "about," when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

In one aspect, the terms "co-administered" and "co-administration" as relating to a subject refer to administering to the subject a compound of the invention or salt thereof along with a compound that may also treat the disorders or diseases contemplated within the invention. In one embodiment, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, subcutaneous, intravenous, oral, aerosol, parenteral, ophthalmic, nasal, pulmonary, and topical administration.

The term "container" includes any receptacle for holding the pharmaceutical composition or to add protection to manage stability and or water-uptake. For example, in one embodiment, the container is the packaging that contains the pharmaceutical composition such as liquid (solution and suspension), semisolid, lyophilized solid, solution, and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a breathing disorder in a patient.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount," and "therapeutically effective amount" refer to a nontoxic but sufficient amount of a compound or agent to provide the desired biological result. That result may be a reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "GM-CSF" refers to granulocyte-macrophage colony-stimulating factor, also known as colony stimulating factor 2 (CSF2). GM-CSF is a monomeric glycoprotein secreted by macrophages, T cells, mast cells, NK cells, endothelial cells, and fibroblasts that functions as a cytokine.

The precursor protein of human GM-CSF has the amino acid sequence of SEQ ID NO:1.

```
        10         20         30         40
MWLQSLLLLG TVACSISAPA RSPSPSTQPW EHVNAIQEAR 50         60         70         80
RLLNLSRDTA AEMNETVEVI SEMFDLQEPT CLQTRLELYK 90        100        110        120
QGLRGSLTKL KGPLTMMASH YKQHCPPTPE TSCATQIITF 130        140
ESFKENLKDF LLVIPFDCWE PVQE
```

The mature protein of human GM-CSF starts at residue 18 of the precursor protein of human GM-CSF, and has the amino acid sequence of SEQ ID NO:2. In certain embodiments, the mature protein is glycosylated. In other embodiments, the protein is monoglycoslyated, diglycosylated, triglycosylated, tetraglycosylated, pentaglycosylated, or hexaglycosylated.

```
        10         20         30         40
APARSPSPST QPWEHVNAIQ EARRLLNLSR DTAAEMNETV 50         60         70         80
EVISEMFDLQ EPTCLQTRLE LYKQGLRGSL TKLKGPLTMM 90        100        110        120
ASHYKQHCPP TPETSCATQI ITFESFKENL KDFLLVIPFD 130        140
CWEPVQE
```

The precursor protein of mouse GM-CSF has the amino acid sequence of SEQ ID NO:3.

```
        10         20         30         40
MWLQNLLFLG IVVYSLSAPT RSPITVTRPW KHVEAIKEAL 50         60         70         80
NLLDDMPVTL NEEVEVVSNE FSFKKLTCVQ TRLKIFEQGL 90        100        110        120
RGNFTKLKGA LNMTASYYQT YCPPTPETDC ETQVTTYADF 130        140
IDSLKTFLTD IPFECKKPGQ K
```

The mature protein of mouse GM-CSF starts at residue 18 of the precursor protein of mouse GM-CSF, and has the amino acid sequence of SEQ ID NO:4.

```
        10         20         30         40
APTRSPITVT RPWKHVEAIK EALNLLDDMP VTLNEEVEVV 50         60         70         80
SNEFSFKKLT CVQTRLKIFE QGLRGNFTKL KGALNMTASY 90        100        110        120
YQTYCPPTPE TDCETQVTTY ADFIDSLKTF LTDIPFECKK 130        140
PGQK
```

Sargramostim, marketed by Genzyme under the tradename Leukine®, is a recombinant GM-CSF that functions as an immunostimulator. Sargramostim has the amino acid sequence of SEQ ID NO:5. In certain embodiments, the protein is glycosylated.

```
        10         20         30         40
APARSPSPST QPWEHVNAIQ EALRLLNLSR DTAAEMNETV 50         60         70         80
EVISEMFDLQ EPTCLQTRLE LYKQGLRGSL TKLKGPLTMM 90        100        110        120
ASHYKQHCPP TPETSCATQI ITFESFKENL KDFLLVIPFD

130
CWEPVQE
```

Molgramostim is a recombinant GM-CSF that functions as an immunostimulatory. Molgramostim has the amino acid sequence of SEQ ID NO:6. In certain embodiments, the protein is not glycosylated.

```
         10          20          30          40
APARSPSPST QPWEHVNAIQ EARRLLNLSR DTAAEMNETV 50          60          70          80
EVISEMFDLQ EPTCLQTRLE LYKQGLRGSL TKLKGPLTMM 90         100         110         120
ASHYKQHCPP TPETSCATQI ITFESFKENL KDFLLVIPFD CWEPVQE
```

In certain embodiments, SEQ ID NO:7 corresponds to the following sequence, wherein the C-terminal residue is Arg (R) or Leu (L):

```
10
QPWEHVNAIQ EA(R/L)
```

In certain embodiments, SEQ ID NO:8 corresponds to the sequence:

```
10
DFLLVIP
```

As used herein, the term "improve" refers to an increase in function, for example, cognitive function, over the level of function exhibited by the animal before administration of the molecules described herein (i.e., GM-CSF and its analogues, mimetics, and derivatives) even if the animal is not exhibiting abnormal function (i.e., is not suffering a disease or condition), but can be considered to be functioning with in the normal range.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The terms "patient," "subject" or "individual" are used interchangeably herein, and refer to any animal, or cells thereof whether in vitro or in situ, amenable to the methods described herein. In a non-limiting embodiment, the patient, subject, or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition, or carrier, such as a liquid or solid filler, stabilizer, dispersing agent, suspending agent, diluent, excipient, thickening agent, solvent, or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose, and sucrose; starches, such as corn starch and potato starch; cellulose, and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

The term "prevent," "preventing," or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein, or the potential to develop a condition contemplated herein, with the purpose to cure, heal, alleviate, relieve, alter, remedy, ameliorate, improve, or affect a condition contemplated herein, the symptoms of a condition contemplated herein or the potential to develop a condition contemplated herein. Such treatments may be specifically tailored or modified, based on knowledge obtained from the field of pharmacogenomics.

The term "specifically bind" or "specifically binds," as used herein, indicates that a first molecule preferentially binds to a second molecule (e.g., a particular receptor or enzyme), but does not necessarily bind only to that second molecule.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application. The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Materials

Unless stated otherwise, materials and compounds were purchased from commercial sources and used without further purification.

Example 1

In order to determine whether a synthetic fragment of GM-CSF or a construct comprising a combination of GM-CSF fragments linked together using PEG linkers is an agonist of the GM-CSF receptor, human cell lines dependent on GM-CSF for proliferation were employed: specifically, the human hematopoietic cell line TF-1 (Hansen, et al., 2008, Cell 134(3): 496-507) and the human cell line MOTE (Monfardini, et al., 2002, Curr Pharm Des 8(24):2185-2199) (both obtained from American Type Culture Collection, or ATCC).

Figure 1B:
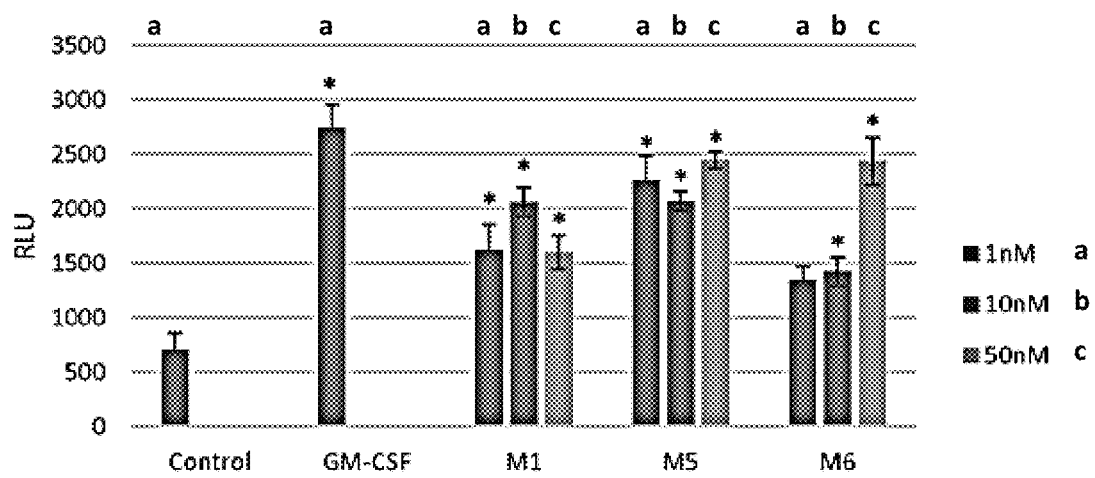

In experiments with the TF-1 cell line, it was determined whether the GM-CSF mimetics of the invention were sufficient to support cell growth and viability in the absence of GM-CSF. Specifically, the cells were grown in medium without GM-CSF (control) as a negative control, in medium supplemented with GM-CSF (GM-CSF; 0.7 nM) as a positive control, or in medium supplemented with one of the GM-CSF mimetics of the invention (i.e., M1, M5, or M6; 1 nM, 10 nM, or 50 nM; FIGS. 1A-1B). Cell viability was measured using the ATPlite assay (PerkinElmer) to determine whether the GM-CSF mimetics of the invention were capable of maintaining the viability of TF-1 cells, which require GM-CSF, thus providing a measure of agonist activity. As shown in FIG. 1A, after a 24 h incubation with TF-1 cells, the GM-CSF mimetics M1, M5, and M6 show GM-CSF receptor agonist activity at 24 h post-treatment; the agonist effect is also replicated at 48 h post-treatment (FIG. 1B).

Example 2

Figure 2A:
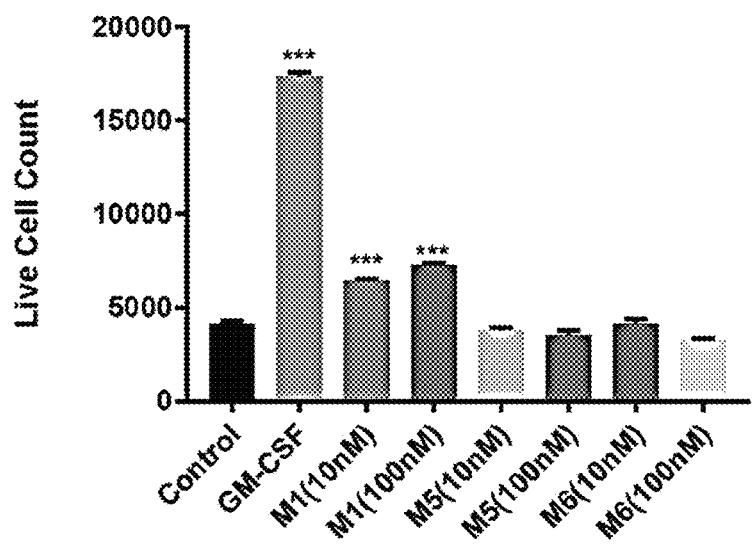
FIGS. 2A-2C illustrate results of experiments wherein the GM-CSF-dependent human erythroleukemic cell line TF-1 was starved of GM-CSF for 24 h prior to treatment with media containing GM-CSF, with medium containing a GM-CSF mimetic (M1, M5 or M6; 10 nM or 100 nM), or with control medium lacking GM-CSF. The cells were fed fresh medium each day to replenish indicated concentrations (10 nM or 100 nM). Live cell counts from 3-4 replicates were plotted for each of the different conditions in FIG. 2A. Error bars represent standard error of the mean. *** indicates $P<0.0001$ are significantly higher than control. The number of live cells grown in the presence of M6 (100 nM) was significantly lower than control at $P<0.042$.
Figure 2B:
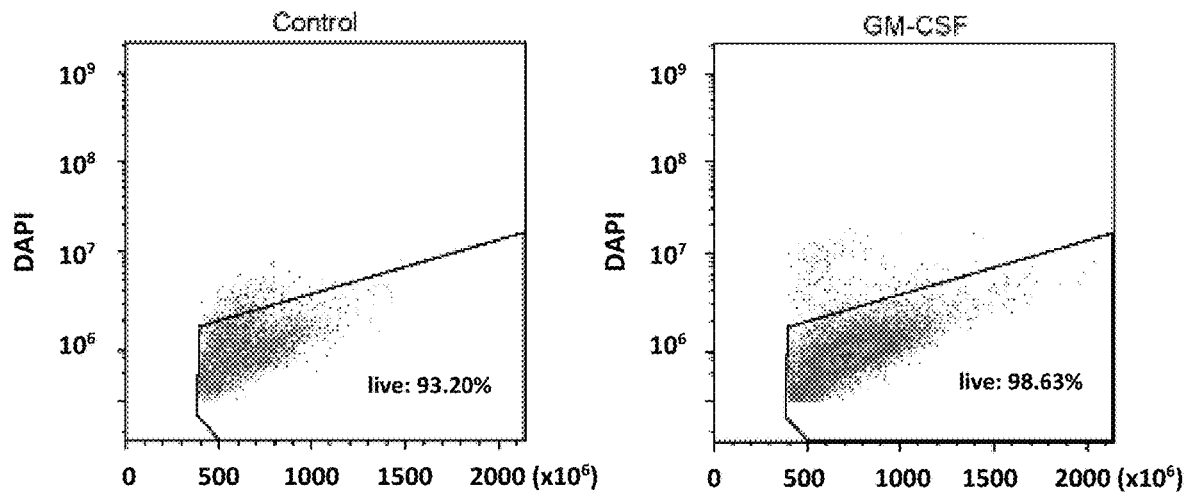
Figure 2B:
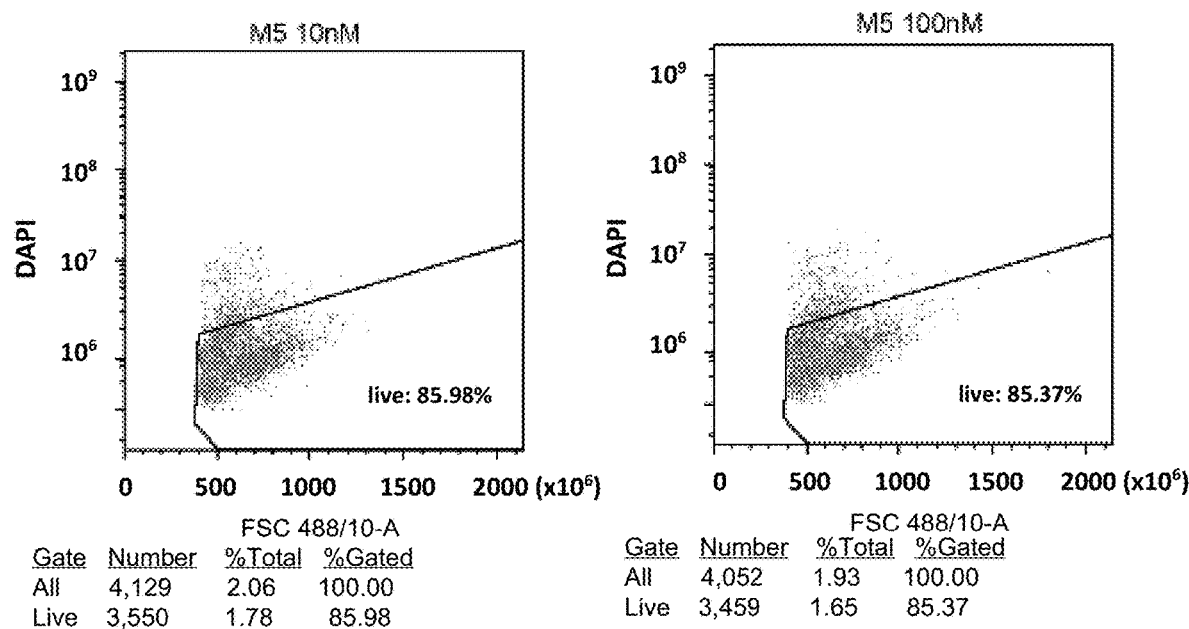
Figure 2C:
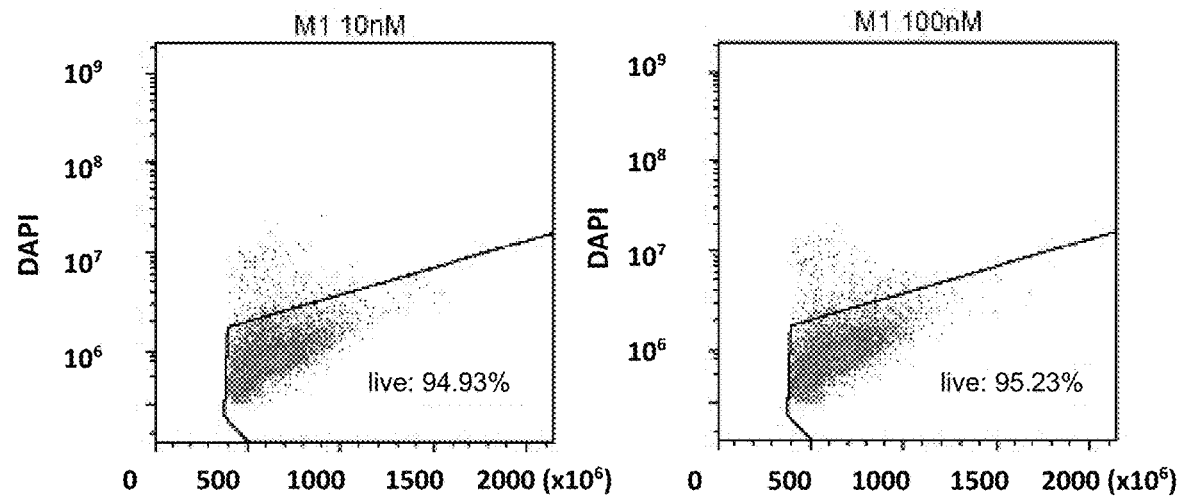
Figure 2C:
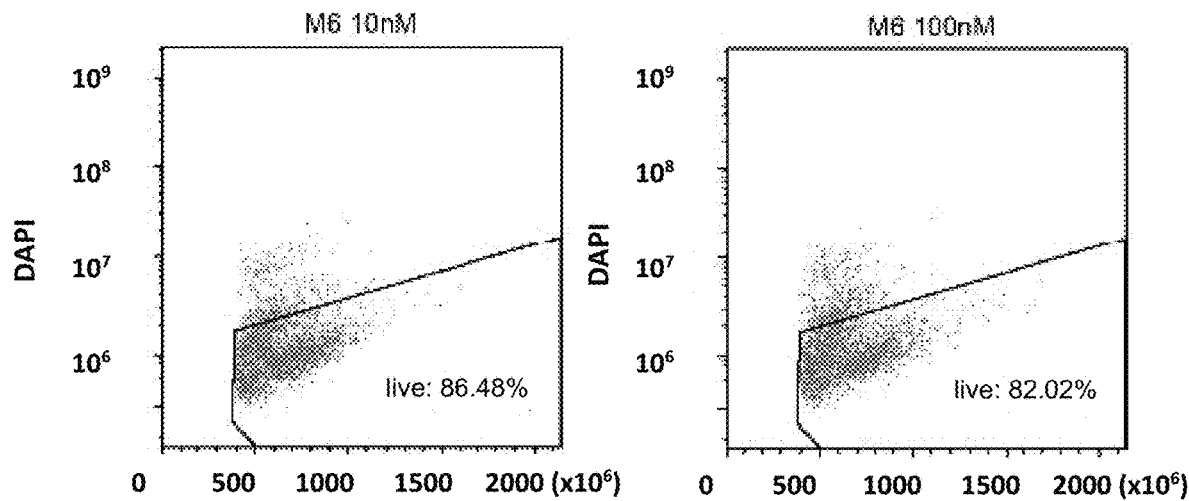

Evaluation of ability of the GM-CSF mimetics to support cell growth was carried out by measuring cell number and cell viability by flow cytometry. The TF-1 cell line was first starved of GM-CSF for 24 h, and then plated in various conditions. TF-1 cells grown in the absence of GM-CSF served as a negative control, and TF-1 cells grown in the presence of GM-CSF served as a positive control (GM-CSF; 0.7 nM). TF-1 cells were also grown in medium containing a GM-CSF mimetic including M1, M5, or M6 (10 nM or 100 nM) (FIGS. 2A-2C). Cells were grown in medium supplemented daily with a dose equal to the initial concentration (nM) of peptide. At 72 h post-treatment, the cells were treated with DAPI (1 μg/ml) to label the nuclei of dead cells and were analyzed on a Yeti cell analyzer from Propel Labs. Cells were initially gated by front and side scatter area to remove debris, and then by front scatter height by front scatter area to isolate single cells. FIG. 2A shows the results of the live cell counts averaged over 3-4 experiments per condition, where M1 shows a significant increase in the cell counts over the negative control (Control). FIGS. 2B-2C show examples of experiments where DAPI-negative (live) cells were plotted by front scatter area. Each dot represents an individual measured cell, and increased color by "heat map" indicates a large group of cells with overlapping DAPI and forward scatter area.

Example 3

Figure 3A:
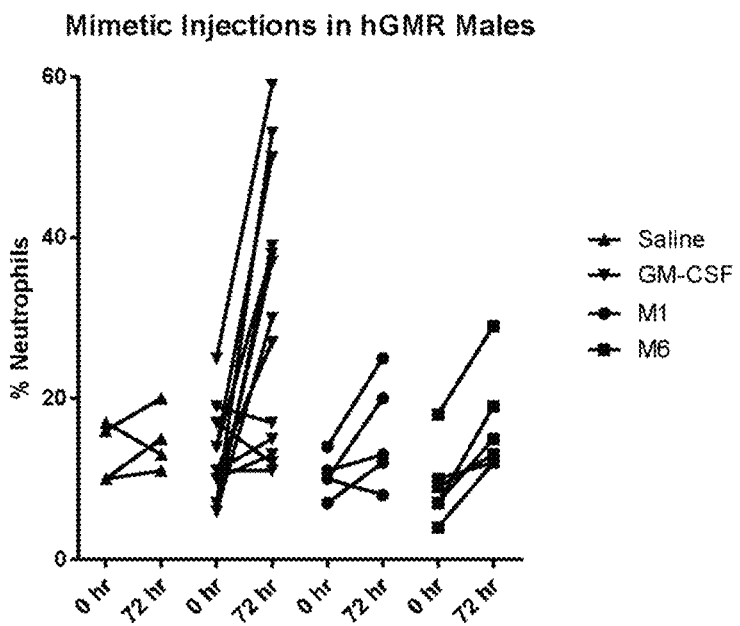
FIGS. 3A-3B comprise a plot illustrating % change in neutrophil levels in blood from transgenic hGMR mice (Nishijima, et al., 1995, Mol. Biol. Cell 6(5):497-508) treated with saline (3 days) as a negative control, with human GM-CSF (hGM-CSF, 5 µg/day×3 days) as a positive control, with the GM-CSF mimetic M1 (M1 5 µg/day×3 days), or with the GM-CSF mimetic M6 (M6, 5 µg/day×3 days) (FIG. 3A). Each connected symbol represents an individual hGMR mouse pre- and post-treatment (0 h and 72 h, respectively).
Figure 3B:
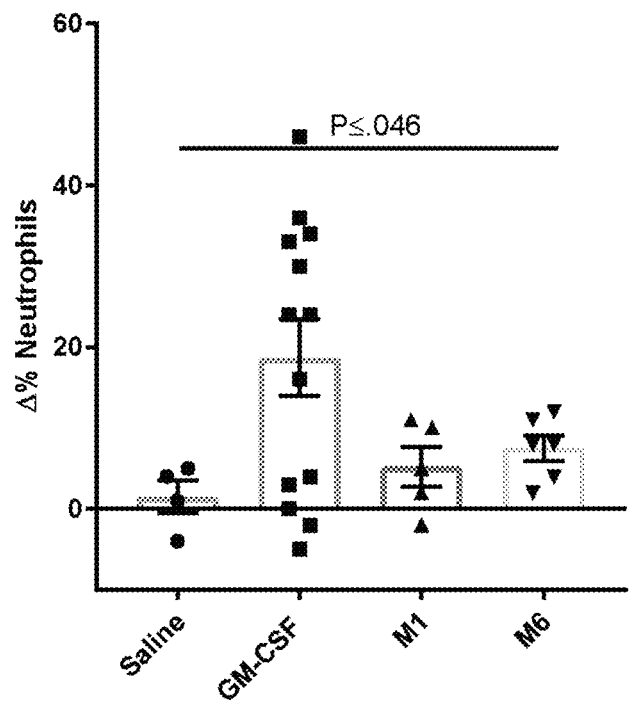

To determine whether the PEG-based GM-CSF mimetics of the invention are active in vivo, the GM-CSF mimetic molecules M1 and M6 were tested in transgenic mice that express the human GM-CSF receptor and are responsive to human GM-CSF, referred to herein as hGMR mice (Nishijima, et al., 1995, Mol. Biol. Cell 6(5):497-508). The hGMR mice were tested for their responses to M1 or M6. Specifically, the study included four groups of mice: (1) hGMR mice injected subcutaneously with saline (n=4 mice) as a negative control (Saline); (2) hGMR mice injected subcutaneously with commercial human GM-CSF (5 ng/animal/day; n=13 mice) as a positive control, because these mice should respond to human GM-CSF; (3) hGMR mice injected subcutaneously with M1 (5 μg/animal/day; n=5 mice); and (4) hGMR mice injected subcutaneously with M6 (5 μg/animal/day; n=6 mice) for three days. Blood samples were collected before the mice received any injections of saline, human GM-CSF, M1, or M6, and blood samples were also collected after the three days of injections. The percentage of neutrophils present in the blood post-treatment was measured by counting from whole blood smears. FIG. 3A illustrates trends in the percentages of neutrophils in individual mice from each of the four groups; each connected symbol represents an individual hGMR mouse pre- and post-treatment (0 h and 72 h, respectively). FIG. 3B compares the changes in the percentage of neutrophils over the course of the treatment for each of the four groups. While many of the injected mice showed trends of increased neutrophils in FIG. 3A, only the combined data for the M6 mimetic was statistically significantly higher than that for the saline control group (P≤0.046), but changes in the percentage of neutrophils in mice treated with either GM-CSF or M6 were statistically significantly higher at 72 h than at 0 h in a paired T-test.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A construct comprising
M1-L-M2, M2-L-M1, M1-L-M1, M2-L-M2, or consecutively-linked combinations of two or more thereof;
wherein:
L is a linker;
M1 consists of a peptide represented by amino acid residues 11-X of SEQ ID NO:2, wherein X is an integer selected from the group consisting of 23, 24, 25, 26, 27, and 28; and
M2 comprises a peptide represented by amino acid residues X-118 of SEQ ID NO:2, wherein X is an integer selected from the group consisting of 103, 104, 105, 106, 107, 108, 109, 110, and 111.

2. The construct according to claim 1, wherein the consecutively-linked combinations of the constructs comprise at least one of:
M1-L-M1-L-M1-L-M1;
M1-L-M1-L-M2-L-M2;
M1-L-M2-L-M2-L-M1;
M2-L-M2-L-M1-L-M1;
M1-L-M2-L-M1-L-M2;
M2-L-M1-L-M2-L-M1;
M2-L-M2-L-M2-L-M2;
M1-L-M1-L-M1-L-M2;
M1-L-M1-L-M2-L-M1;
M1-L-M2-L-M1-L-M1;
M2-L-M1-L-M1-L-M1;
M2-L-M2-L-M2-L-M1;
M2-L-M2-L-M1-L-M2;
M2-L-M1-L-M2-L-M2;
M1-L-M2-L-M2-L-M2; and
M2-L-M1-L-M2-L-M2.

3. The construct according to claim 1, wherein M1 consists of residues 11-28 of SEQ ID NO:2 (QPWEHVNAIQEARRLLNL).

4. The construct according to claim 1, wherein M2 comprises residues 103-118 of SEQ ID NO:2 (FESFKENLKDFLLVIP).

5. The construct according to claim 1, wherein the construct comprises M1-L-M2 or M2-L-M1 and M1 consists of residues 11-28 of SEQ ID NO:2 (QPWEHVNAIQEARRLLNL).

6. The construct according to claim 1, wherein the construct comprises M1-L-M2 or M2-L-M1 and M2 comprises residues 103-118 of SEQ ID NO:2 (FESFKENLKDFLLVIP).

7. The construct according to claim 1, wherein M1 consists of a peptide represented by amino acid residues 11-X of SEQ ID NO:2, wherein X is an integer selected from the group consisting of 23, 24, 25, 26, 27, and 28 and wherein amino acid position 23 is a leucine.

8. The construct according to claim 1, wherein each L comprises a polypeptide, polyethylene glycol (PEG), or a derivative thereof.

9. The construct according to claim 1, wherein when each L is PEG or a derivative thereof, the PEG or derivative thereof comprises $(CH_2CH_2O)n$ wherein n is an integer from 2 to 30.

10. The construct according to claim 1, wherein when L is a polypeptide, the polypeptide comprises $(G4S)n$, $(G)m$ or $(A)m$, wherein n is an integer ranging from 1 to 6 and m is an integer ranging from 1 to 200.

11. The construct according to claim 1, wherein Lin at least one occurrence is a peptide linker $(G_4S)n$, $(G)_m$ or $(A)_m$, wherein n is an integer ranging from 1 to 6, and each occurrence of m is independently an integer ranging from 1 to 200.

12. The construct according to claim 1, wherein L comprises a hairpin linker.

13. The construct according to claim 1, wherein L is $(CH_2CH_2O)n$ wherein n is 4, 6, or 8.

14. The construct according to claim 1, wherein the construct is part of a composition, and the composition further comprises a pharmaceutically acceptable carrier or excipient.

15. A method for using the composition according to claim 14 to treat a subject in need of Granulocyte-macrophage colony-stimulating factor (GM-CSF) therapy.

16. The method of claim 15, wherein using the composition to treat the subject comprises administering the composition subcutaneously, by inhalation, orally, intranasally, rectally, parenterally, sublingually, transdermally, transmucosally, intravesically, intrapulmonarily, intraduodenally, intragastrically, intrathecally, epidurally, intrapleurally, intraperitoneally, intratracheally, otically, intraocularly, intramuscularly, intradermally, intra-arterially, intravenously, intrabronchially, or topically to the subject.

17. The method according to claim 16, wherein the subject is a mammalian subject.

18. A kit comprising the constructs of claim 1; and at least one container.

19. The method of claim 15, wherein the subject comprises a subject in need of neurite outgrowth or neurogenesis, in need of promoting myeloid reconstitution, having neuronal loss; having a traumatic brain injury (TBI), in need of improving cognition, in need of stabilizing cognition, in need of reversing loss of cognition; in need of increasing or stabilizing neutrophil levels, having type I or type 2 diabetes, having or developing chemobrain, having Down Syndrome (DS), having Alzheimer's Disease (AD), having Parkinson's Disease, or having cerebral palsy, or a combination thereof.

20. The construct according to claim 1, wherein the construct is M1-L-M2-L-M2-L-M1.

21. The construct according to claim 20, wherein L is polyethylene glycol (PEG).

22. The construct according to claim 21, wherein M1 is amino acid residues 11-23 of SEQ ID NO:2 (QPWEHVNAIQEAR) and M2 is amino acid residues 112 to 118 of SEQ ID NO:2 (DFLLVIP).

23. The construct according to claim 20, wherein the middle linker, L, is PEG and the PEG is PEG8.

24. The method of claim 15, wherein the subject is a subject in need of at least one of, improving cognition, stabilizing cognition, and reversing loss of cognition.

25. The method of claim 15, wherein the subject is a subject having at least one of Type 2 diabetes, Alzheimer's Disease (AD), Parkinson's Disease and Down's Syndrome.

* * * * *

```
                              SEQUENCE LISTING

<160> NUMBER OF SEQ ID NOS: 8

<210> SEQ ID NO 1
<211> LENGTH: 144
<212> TYPE: PRT
<213> ORGANISM: Artificial Sequence
<220> FEATURE:
<223> OTHER INFORMATION: Chemically synthesized;  precursor protein of
      human GM-CSF

<400> SEQUENCE: 1

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 2
<211> LENGTH: 127
<212> TYPE: PRT
<213> ORGANISM: Artificial Sequence
<220> FEATURE:
<223> OTHER INFORMATION: Chemically synthesized;  mature protein of
      human GM-CSF

<400> SEQUENCE: 2

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60
```

```
Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 3
<211> LENGTH: 141
<212> TYPE: PRT
<213> ORGANISM: Artificial Sequence
<220> FEATURE:
<223> OTHER INFORMATION: Chemically synthesized; precursor protein of
      mouse GM-CSF

<400> SEQUENCE: 3

Met Trp Leu Gln Asn Leu Leu Phe Leu Gly Ile Val Val Tyr Ser Leu
  1               5                  10                  15

Ser Ala Pro Thr Arg Ser Pro Ile Thr Val Thr Arg Pro Trp Lys His
                 20                  25                  30

Val Glu Ala Ile Lys Glu Ala Leu Asn Leu Leu Asp Asp Met Pro Val
            35                  40                  45

Thr Leu Asn Glu Glu Val Glu Val Val Ser Asn Glu Phe Ser Phe Lys
        50                  55                  60

Lys Leu Thr Cys Val Gln Thr Arg Leu Lys Ile Phe Glu Gln Gly Leu
 65                  70                  75                  80

Arg Gly Asn Phe Thr Lys Leu Lys Gly Ala Leu Asn Met Thr Ala Ser
                 85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Gly Gln Lys
130                 135                 140

<210> SEQ ID NO 4
<211> LENGTH: 124
<212> TYPE: PRT
<213> ORGANISM: Artificial Sequence
<220> FEATURE:
<223> OTHER INFORMATION: Chemically synthesized; mature protein of
      mouse GM-CSF

<400> SEQUENCE: 4

Ala Pro Thr Arg Ser Pro Ile Thr Val Thr Arg Pro Trp Lys His Val
  1               5                  10                  15

Glu Ala Ile Lys Glu Ala Leu Asn Leu Leu Asp Asp Met Pro Val Thr
                 20                  25                  30

Leu Asn Glu Glu Val Glu Val Val Ser Asn Glu Phe Ser Phe Lys Lys
            35                  40                  45

Leu Thr Cys Val Gln Thr Arg Leu Lys Ile Phe Glu Gln Gly Leu Arg
        50                  55                  60

Gly Asn Phe Thr Lys Leu Lys Gly Ala Leu Asn Met Thr Ala Ser Tyr
 65                  70                  75                  80

Tyr Gln Thr Tyr Cys Pro Pro Thr Pro Glu Thr Asp Cys Glu Thr Gln
                 85                  90                  95
```

Val Thr Thr Tyr Ala Asp Phe Ile Asp Ser Leu Lys Thr Phe Leu Thr
            100                 105                 110

Asp Ile Pro Phe Glu Cys Lys Lys Pro Gly Gln Lys
        115                 120

<210> SEQ ID NO 5
<211> LENGTH: 127
<212> TYPE: PRT
<213> ORGANISM: Artificial Sequence
<220> FEATURE:
<223> OTHER INFORMATION: Sargramosti

<400> SEQUENCE: 5

Ala Pro Ala Arg Ser Pro Ser Pro Ser Thr Gln Pro Trp Glu His Val
1               5                   10                  15

Asn Ala Ile Gln Glu Ala Leu Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 6
<211> LENGTH: 127
<212> TYPE: PRT
<213> ORGANISM: Artificial Sequence
<220> FEATURE:
<223> OTHER INFORMATION: Molgramostim

<400> SEQUENCE: 6

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 7
<211> LENGTH: 12
<212> TYPE: PRT

```
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (12)..(12)
<223> OTHER INFORMATION: Arg or Leu

<400> SEQUENCE: 7

Gln Pro Trp Glu His Val Asn Ala Ile Gln Glu Xaa
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 8

Asp Phe Leu Leu Val Ile Pro
1               5
```

UNITED STATES PATENT AND TRADEMARK OFFICE
CERTIFICATE OF CORRECTION

PATENT NO.         : 11,993,638 B2                           Page 1 of 1
APPLICATION NO.    : 17/589154
DATED              : May 28, 2024
INVENTOR(S)        : Huntington Potter et al.

It is certified that error appears in the above-identified patent and that said Letters Patent is hereby corrected as shown below:

In the Claims

In Claim 11, Column 36, Line 45, replace "Lin" with "L in" prior to 'at'.

Signed and Sealed this
Twenty-sixth Day of November, 2024

Katherine Kelly Vidal
*Director of the United States Patent and Trademark Office*